United States Patent [19]

Browning

[11] 4,197,845
[45] Apr. 15, 1980

[54] DEVICE FOR THE PREVENTION OF DECUBITUS ULCERS ON THE HUMAN HEEL

[76] Inventor: Edward G. Browning, 1203 E. Dear, Kirksville, Mo. 63501

[21] Appl. No.: 912,402

[22] Filed: Jun. 5, 1978

[51] Int. Cl.² .......................................... A61B 19/00
[52] U.S. Cl. ................................. 128/149; 128/153
[58] Field of Search ....................... 128/149, 153, 80 R

[56] References Cited

U.S. PATENT DOCUMENTS

| | | | |
|---|---|---|---|
| 3,308,491 | 3/1967 | Spence | 128/153 X |
| 3,406,683 | 10/1968 | Steinberg | 128/153 X |
| 3,689,948 | 9/1972 | Graves et al. | 128/149 X |
| 3,937,218 | 2/1976 | Gaylord, Jr. | 128/80 R |
| 4,076,022 | 2/1978 | Walker | 128/149 |

FOREIGN PATENT DOCUMENTS 686613  5/1964  Canada ..................................... 128/149

*Primary Examiner*—John D. Yasko
*Attorney, Agent, or Firm*—Glen R. Simmons

[57] ABSTRACT

The invention relates to an apparatus for the preparation of decubitus ulcers on the human heel, said apparatus including a harness adapted to fit about the human foot and ankle, with said apparatus having a reservoir-cushion connected thereto such that when the user of the device is lying on his/her back the reservoir-cushion is positioned between the back of said user's ankle and the surface on which said user reposes causing the human heel to remain suspended above the surface on which said user reposes and therefore removes all pressure from the human heel.

6 Claims, 3 Drawing Figures

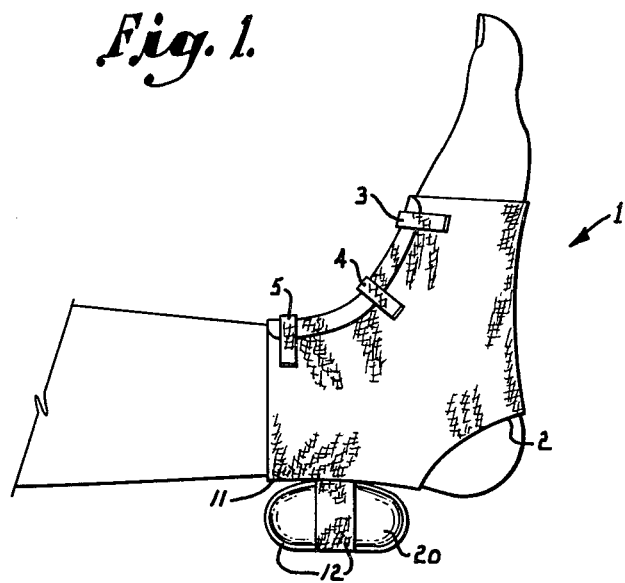
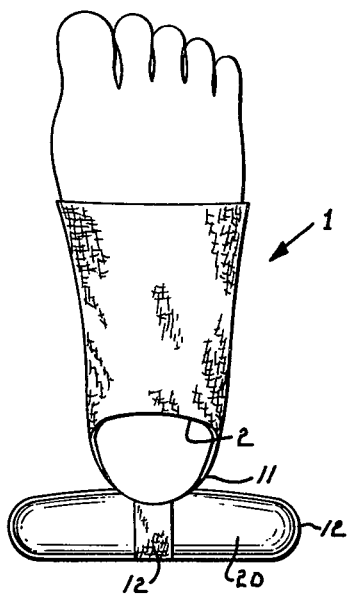
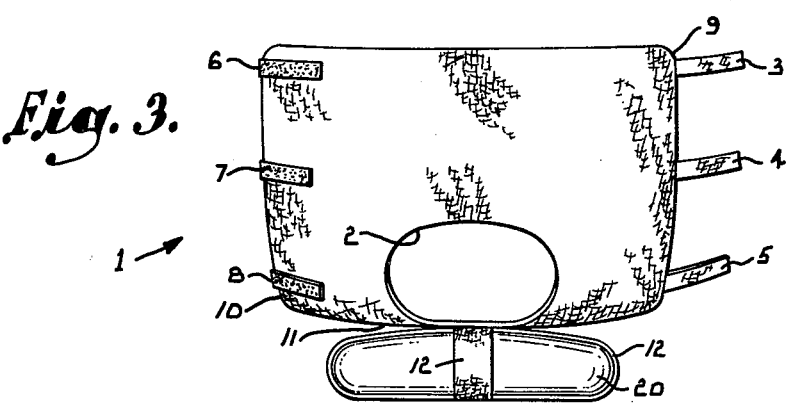

DEVICE FOR THE PREVENTION OF DECUBITUS ULCERS ON THE HUMAN HEEL

BACKGROUND OF THE INVENTION AND OBJECTS

For generations, decubitus ulcers have continued to be a perplexing problem for bed patients and physicians alike. Decubitus ulcers or pressure sores are ulcerations caused by prolonged pressure in a patient confined to bed for a long period of time. Particularly perplexing to bed patients and physicians are the predictable pressure sores which appear on the pressure points of the body i.e., backs of heels, legs, buttocks, over the sacrum, elbows and scapula after a patient has been bedfast for an extended period.

Heretofore, the only consistent manner of preventing the occurrence of decubitus ulcers on the back of the human heel, leg and other pressure points noted hereinabove, was to alter the patient's position from back to front to side to back, etc. or some variation thereof at regular intervals. To date, there has been no satisfactory way of preventing the appearance of decubitus ulcers on the back of a patient's heels.

Therefore, it is an object of the present invention to provide an apparatus for the prevention of decubitus ulcers on the back of the human heel.

It is a further object of this invention to provide an apparatus, including a harness which fits on or around and about the human heel and a portion of the human foot and human ankle which apparatus aids in preventing the formation of decubitus ulcers or pressure sores on the back of the human heel.

It is a further object of this invention to provide an apparatus, including a harness which fits on or about the human ankle and foot including a reservoir-cushion attached to said harness on which reservoir-cushion the back of the human ankle can rest while the patient is in bed to prevent the formation of pressure sores on the back of the human leg and heel area.

It is a further object of this invention to provide an apparatus, including a reservoir-cushion on which the back of the human ankle of a bedfast patient can rest in order to prevent the formation and development of decubitus ulcers on the back of the human heel.

It is a further object of this invention to provide an apparatus for the prevention of decubitus ulcers on the human foot.

It is a further object of this invention to provide an apparatus for the prevention of decubitus ulcers on the human foot by the use of cushion means in combination with a harness adapted to fit about the human ankle.

It is a further object of this invention to provide an apparatus for the prevention of decubitus ulcers on the human foot by the use of cushion means in combination with a harness adapted to fit about the human ankle and foot.

It is a further object of the present invention to provide an apparatus for the prevention of decubitus ulcers on the human foot which apparatus is adapted to be securely held about the user's foot and ankle by the user of Velcro fasteners.

It is a further object of the present invention to provide an apparatus for the prevention of decubitus ulcers on the human foot which apparatus is adapted to be securely held about the user's foot and ankle by the use of lace-up means.

It is a further object of the present invention to provide an apparatus for the prevention of decubitus ulcers on the human foot which apparatus is adapted to be securely held about the user's foot and ankle by the user of draw-string means.

It is a further object of the present invention to provide an apparatus for the prevention of decubitus ulcers on the human foot which apparatus is adapted to be securely held about the user's foot and ankle by the user of zipper means.

FIG. 1 is a side view of the device of the invention while employed on a bed patient's foot.

FIG. 2 is a view toward the bottom of the foot of a patient on which the device of the invention is employed.

FIG. 3 is a view of the device of the invention as it appears in an open-unemployed position.

DESCRIPTION OF THE PREFERRED EMBODIMENT

Referring now to FIG. 1 of the drawings there is seen the device of the invention as employed on the foot of a bed patient. The device includes a harness, generally denoted as 1, shaped in the form of the ankle area and preferably sewn together from pieces of a soft, yet strong material such as cotton. The ankle harness includes a cut-out portion 2 as seen in FIGS. 1, 2 and 3 to allow for ventilation on the tip of the heel. The device further includes Velcro fasteners 3, 4 and 5 and corresponding parts 6, 7 and 8 with parts 3, 4 and 5 connected for example by a sewing process to one side 9 of the device and with matching parts 6, 7 and 8 attached to opposite flap 10 as seen in the open position in FIG. 3. To the back portion of the device 11 there is attached by a sewing or other suitable process straps 12. Straps 12 criss-cross themselves with each circling reservoir-cushion 20. Reservoir-cushion 20 is preferably made of flexible plastic water-tight and air-tight material and encloses a reservoir of fluid which may be either compressed air or water. The reservoir-cushion 20 is preferably somewhat longer than it is wide and generally in the area of 6 inches long, approximately 2½ inches wide and approximately 1½ to 2 inches thick providing for approximately 250 cc's of fluid in the reservoir. However, these dimensions may be altered and yet be within the scope of applicant's invention. Therefore, it will be seen that reservoir-cushion 20 via strap 12 is securely affixed to the back of harness 1 to the portion 11 of said harness which during times the device is in use comes in contact with the back of the user's ankle.

Thus, it will be seen that when the bed patient user places the device around his foot and ankle as seen in FIGS. 1 and 2 reservoir-cushion 20 is securely affixed to the back ankle portion of said device. The reservoir-cushion serves as a spacer and keeps the user's ankle and heel off the surface on which the user reposes. This arrangement has been found to prevent the formation of decubitus ulcers or pressure sores on the backs of the heels and lower extremity of bedfast patients as well as patients who are not bedfast but may ambulate only occasionally.

It will become apparent to the reader that the harness about the user's foot could take various other forms yet maintain the reservoir-cushion in the respective position to the user's foot all within the scope of the applicant's device.

It will become apparent to the reader that this device also allows the patient user much freedom of movement in that the harness keeps the reservoir-cushion in correct position about the ankle. The device, therefore, does not need to be removed should the patient be permitted to ambulate. Upon the user returning to the supine position the device automatically assumes the protective position on the ankle.

Further, it will become apparent to the reader that materials other than compressed air or entrapped water may be employed in the cushion.

While the device has been described with the reservoir-cushion positioned on the part of its harness in contact with the back of the user's ankle, obviously, the reservoir-cushion could be attached to any other part of the harness as needed to space that respective portion of the user's foot above the surface on which the user reposes. For example, should the user be required to lie on his/her side, the reservoir-cushion could readily be attached to the respective side of the user's foot nearest the surface on which the user reposes to space said side from said surface. Likewise, said reservoir-cushion could be attached to a part of the harness on top of the user's foot for patients who must lie face down while in bed to keep the top of the user's foot spaced from the surface on which the user reposes.

Further, it should be noted that cushion 20 could be other than a fluid filled reservoir i.e., the cushion could be made of light-weight, deformable material such as foam rubber or sponge material which, even though compressed, would nonetheless provide the desired spacing when compressed between the user's foot and the surface on which said user reposes.

The fasteners could be other than Velcro e.g., a lace-up, draw-string or zipper fastener could be employed as means to hold the harness and cushion in place on the user's foot as desired and yet be within the scope of the applicant's invention.

Having fully described my invention I claim:

1. A device for the prevention of decubitus ulcers comprising:
   a. an ankle harness means for the human ankle; said ankle harness means being shaped in the form of the human ankle area and being formed only of soft flexible material; said harness means having a cut-out portion which permits the heel of the user of the device to be open to the atmosphere to allow for ventilation; said ankle harness means being sized and shaped such that when positioned for usage around an ankle area of the user, edges of said ankle harness means overlap each other on the front side of the ankle;
   b. fastener means attached to said harness means in proximity to said edges for securely holding said harness means on the ankle area of the user's foot on which the device is employed;
   c. cushion means attached to said harness means for causing the device user's heel and back ankle area on which said device is placed to be suspended above the surface on which said user reposes while lying on his/her back; said cushion means being only attached to and in contact with a portion of said harness means on the back of the user's ankle with said only point of attachment and contact being spaced upwardly along the back of the user's ankle from the user's heel; said cushion means thus being securely fastened to said harness means at a point which permits the heel of the ankle on which the device is employed to be free of any pressure from the device or surface on which the user reposes.

2. The device of claim 1 wherein said fastener means is at least one Velcro fastener means.

3. The device of claim 1 wherein said fastener means includes a lace-up or draw-string means for securely holding said harness on the ankle area of the user's foot on which the device is employed.

4. The device of claim 1 wherein said cushion means is a sealed reservoir containing fluid.

5. The device of claim 1 wherein said cushion means includes foam rubber means.

6. The device of claim 1 wherein said cushion means includes sponge means.

* * * * *